(12) United States Patent
Viller et al.

(10) Patent No.: US 8,012,200 B2
(45) Date of Patent: Sep. 6, 2011

(54) ENDOVASCULAR MAGNETIC METHOD FOR TARGETED DRUG DELIVERY

(76) Inventors: Alexander G. Viller, Moscow (RU); Andrey Buryakov, Moscow (RU)

( * ) Notice: Subject to any disclaimer, the term of this patent is extended or adjusted under 35 U.S.C. 154(b) by 239 days.

(21) Appl. No.: 12/442,731

(22) PCT Filed: Sep. 26, 2006

(86) PCT No.: PCT/RU2006/000496
§ 371 (c)(1),
(2), (4) Date: Mar. 25, 2009

(87) PCT Pub. No.: WO2008/039091
PCT Pub. Date: Apr. 3, 2008

(65) Prior Publication Data
US 2010/0036480 A1    Feb. 11, 2010

(51) Int. Cl.
*A61F 2/06* (2006.01)
(52) U.S. Cl. ..................................... 623/1.42
(58) Field of Classification Search .................. None
See application file for complete search history.

(56) References Cited

U.S. PATENT DOCUMENTS

| | | | |
|---|---|---|---|
| 5,921,244 A * | 7/1999 | Chen et al. | 128/897 |
| 7,101,394 B2 * | 9/2006 | Hamm et al. | 623/1.42 |
| 2001/0047185 A1 * | 11/2001 | Satz | 606/198 |
| 2006/0041182 A1 * | 2/2006 | Forbes et al. | 600/12 |

FOREIGN PATENT DOCUMENTS

| | | |
|---|---|---|
| FR | 2737969 | 1/1998 |
| RU | 2121317 | 11/1998 |

* cited by examiner

*Primary Examiner* — David Isabella
*Assistant Examiner* — Brian Dukert
(74) *Attorney, Agent, or Firm* — Bardmesser Law Group

(57) ABSTRACT

The method for endovascular magnetic targeting drug delivery in a vascular wall and adjoining tissues, wherein an endovascular mesh stent with paramagnetic properties is preliminary implanted in the area of interest by a catheter, a polymeric magneto-responsive carrying agent in the form of particles, containing a drug, is injected, and a magnetic field is applied, characterized in that, at least, one temporary catheter is introduced in the right atrium, and/or in ventricles of heart, and/or in a coronary sinus and/or in a coronary vein, which distal end takes a position close to the implanted mesh stent, thereupon, a gradient permanent magnetic field is generated and adjusted by means of a permanent magnet and/or a solenoid with the core, connected to an electric power source, which magnet or solenoid are located at the distal end of each temporary catheter, where the maximal gradient of magnetic field is located in the implanted endovascular stent, principally on the stent mesh.

20 Claims, 5 Drawing Sheets

ENDOVASCULAR MAGNETIC METHOD FOR TARGETED DRUG DELIVERY

CROSS REFERENCE TO RELATED APPLICATIONS

This application is a U.S. National Phase of PCT/RU2006/000496, filed on Sep. 26, 2006, the entire contents of which are hereby incorporated by reference.

BACKGROUND OF THE INVENTION

The invention relates to medicine, namely to methods of endovascular drug therapy, and, in particular, to methods of locally increasing a concentration of drugs in the walls of arteries and veins, in particular for prevention of coronary restenosis.

A number of drugs require intravenous or intra-arterial infusion, by passing the digestive system, so as to preserve the drugs from degradation by catalytic enzymes in the digestive tract. Also, application of a drug with high toxicity in high concentration requires accurate control of their delivery. Moreover, a delivery agent, not being an active pharmacological agent, can still boost the activity of the delivered drug by mediation of its therapeutic activity.

At present, the role of a delivery agent is usually played by a stent with a drug coating. The active substance (paclitaxel, sirolimus, zotarolimus) is dissolved in the polymeric coating of the stent, and is then gradually released, preventing proliferation of smooth muscle cells of an arterial wall, thus preventing evolution and occurrence of restenosis of the stented arteries. At the same time, the drug eluting stents induce an inflammation and can even result in subsequent thrombosis owing to secondary hypersensitivity in some patients, and also owing to a slowdown of endothelization process (see N. Malik et al., "Phosphorylcholine-coated stents in porcine coronary arteries: in vivo assessment of biocompatibility," *J Invasive Cardiol.* 13 (2001), pp. 193-201, A. V. Finn et al., "Differential response of delayed healing and persistent inflammation at sites of overlapping sirolimus- or paclitaxel-eluting stents," *Circulation* 112 (2005), pp. 270-278, R. Virmani et al., "Localized hypersensitivity and late coronary thrombosis secondary to a sirolimus-eluting stent: should we be cautious?" *Circulation* 109 (2004), pp. 701-705). The polymeric coating extends the stage of thrombogenesis and of acute inflammation. All existing intravascular stents used in a clinical practice, have paramagnetic properties, except for diamagnetic nitinol self-expandable stents.

There are alternate ideas of a drug delivery to a vascular wall, in particular, by using composite super-paramagnetic nanoparticles, the ferromagnetic or paramagnetic stents and an exterior magnetic field. At the same time, some data are available about negative biological effects on humans of the impact of a permanent magnetic field with the intensity over 1 Tesla (see Y. Kinouchi, "Electromagnetic Mechanisms of Biomagnetic Effects," *The Journal of the Japanese Society of Magnetic Applications in Dentistry*, (1997) Vol. 6, No. 1, pp. 13-17). Several comprehensive reviews have attempted to postulate human exposure limits and recommends a level of 0.02 T for continuous exposure. The apparent basis for the 0.02 T recommendation derives from the fact that lowest exposure level which no effect was reported was 0.008-0.01 T (see E. E. Ketchen et al., "The Biological Effects of Magnetic Fields on Man," *Am. Ind. Hyg. Assoc. J.*, 39:1-11 (1978) and Z. N. Nakhilnitskaya, "Biological Effects of Permanent Magnetic Fields," *Space Biology and Aerospace Medicine*, 8(6): 1-25 (1974)). Two general types of effects from exposures to magnetic fields are postulated as a result of theoretical calculations: magnetomechanical and electromagnetic. Magnetomechanical forces could produce translation and rotation of particles (molecules, cells, etc.), and electromagnetic forces could produce induced voltages and flow modification.

A magnet-controlled system of the targeted drug delivery to destination places, associated with magneto-sensitive particles (see U.S. Patent Publication No. 2006/0041182), where an intravascular magnetized device (for example, a stent made of a paramagnetic material) is implanted, in advance, by a catheter, in the area of interest of the blood vessel, then a polymeric magneto-sensitive carrying agent prepared in the form of particles containing a drug, is injected into the blood vessel, and thereafter, a magnetic field from an exterior source is activated, whereby a gradient magnetic field is generated in the area of interest of the blood vessel, attracting particles of the magneto-sensitive carrying agent.

However, this method cannot be used in organs and vessels with an intensive blood flow. In particular, the aorta and coronary arteries of heart have such high parameters of volumetric velocity of a blood flow, that particles of the carrying agent with size range 0.01 to 1.0 microns will only concentrate in the field of interest in case of the magnetic field induction in excess of 1.0 Tesla. This is unpredictable for the cardiac electrophysiology, for functioning of pace-makers of heart rhythm and carries a risk generating life-threatening arrhythmias. Also, the unpredictable Theological effects caused by concentration of erythrocytes are possible in the area in question. For the particles containing drug with size range 2 to 10 microns, i.e., comparable to size of the blood cell components, concentration on magnetosensitive implants under the force of an exterior magnetic field can result in magneto-induced thrombogenesis. Also, a strong exterior permanent magnetic field has an impact on the central nervous system.

A conventional method of use of a ring catheter (see U.S. Pat. Nos. 5,951,566 and 5,851,218), intended for slow expansion of walls at vasoconstriction without blocking a fluid stream and/or the drainage of sediments on the walls of blood vessels, is known. The method consists of an introduction of a catheter with a conductor of a magnetic field and an inductance coil, and delivery to the area of interest, along with the catheter, of a stent coated with activatable adhesives and provided with elements containing permanent magnets. Interacting of magnetic fields of the inductance coil and of the permanent magnets allows to expand the stent and to intensify the process of implantation of adhesive specimens in the walls of the blood vessel. However, in such an arrangement, the magnetized micro-carrying agents will be attracted to an element with the maximum magnetic intensity, i.e., to the catheter and its components (to the coil core and/or to the ring permanent magnet), instead of the stent on walls of the blood vessel. Thus, it will not be possible to use these micro-carrying agents for intensification of treating the walls of the blood vessel with the drugs. This known method is inapplicable to processing intravascular areas with magneto-sensitive carrying agents containing a drug.

SUMMARY OF THE INVENTION

The claimed invention is intended to eliminate the above drawbacks.

The technical result, achieved by application of the claimed method, consists in increased reliability, efficiency and safety of delivery of drugs to a vascular wall and adjoining tissues in the vessels with an intensive stream of blood in the area of implantation of the stent, both at the time of stent implantation, and at a substantially later time, and in particular, in coronary arteries.

Still another technical result of the claimed method consists in lowering the risk of restenosis of arteries in the area of the implanted stent owing to more effective drug administration.

Also, the proposed method is aimed at controlling concentration of the drugs in a vascular wall by means of adjustment of the magnetic field parameters.

The proposed method includes that, for endovascular delivery of a drug in a vascular wall and adjoining tissues in the area of implantation of a stent with paramagnetic properties, a polymeric magneto-responsive carrying agent in the form of particles, containing a drug, is injected. At this moment, a gradient permanent magnetic field is generated and adjusted by means of at least one temporary catheter containing at its distal end, a permanent magnet and/or a solenoid with the core, connected to an electric power source, where the temporary catheter is introduced into the right auricle, and/or into ventricles of heart, and/or into a coronary sinus and/or into a coronary vein, and the maximal gradient of the magnetic induction density is located in the stented arterial segment, thus providing improved settling and deduction of magnetosensitive particles to the inner wall of the blood vessel in the area of the paramagnetic stent implantation.

It is preferable to use, for efficient control of the magnetic field gradient, a solenoid with a core of cylindrical shape, covered by a conical cap, or a permanent magnet of the same shape.

The level of the magnetic induction density of the volumetric gradient magnetic field is adjusted by varying the electric current parameters in the solenoid or by selection of proper permanent magnets.

The effective aiming of the magnetic gradient is implemented by controlled positioning of the inner magnetic sources regarding the stent. Shaping of a three-dimensional permanent gradient magnetic field is also possible.

The stent is made of a paramagnetic material, such as commonly used paramagnetic alloys: steel 316L, cobalt-chromium alloy, cobalt-nickel alloy, etc. Application of biodegradable stents with paramagnetic properties is also possible.

The size of particles of a polymeric magneto-responsive carrying agent is, preferably within the range 0.01 to 1.0 micron.

At the distal end of the temporary catheter, a cylindrical permanent magnet with the typical length range 1 to 50 mm is used.

At the distal end of the temporary catheter, a cylindrical solenoid with the length range 1 to 50 mm can be used, as another alternative.

BRIEF DESCRIPTION OF THE DRAWINGS

For better understanding of the claimed invention, its detailed description with corresponding drawings follows.

FIG. 2 shows source 2 of electric current which is necessary in case of using the solenoid in the temporary magnetic catheter 3. Also, a cardiac vein 6 through which the temporary magnetic catheter 3 is introduced, is shown and coronary artery 5, which accommodates stent 4.

DETAILED DESCRIPTION OF THE PREFERRED EMBODIMENTS

Figure 1:
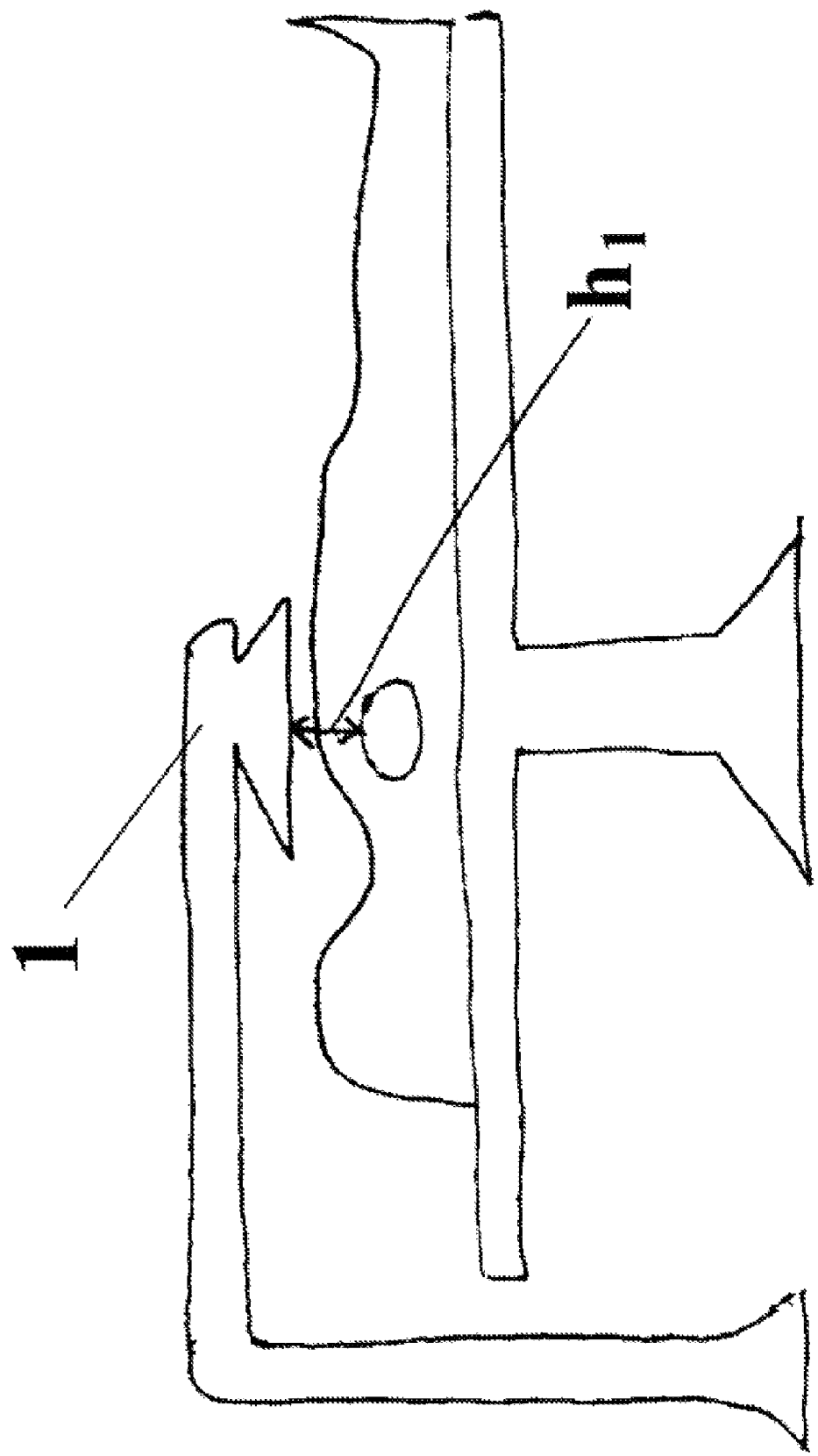
FIG. 1 shows the conventional method with application of an exterior magnetic field, where 1 is an exterior source of a magnetic field, hi is the distance to a stent, which is usually the range of 50 to 100 mm.
Figure 2:
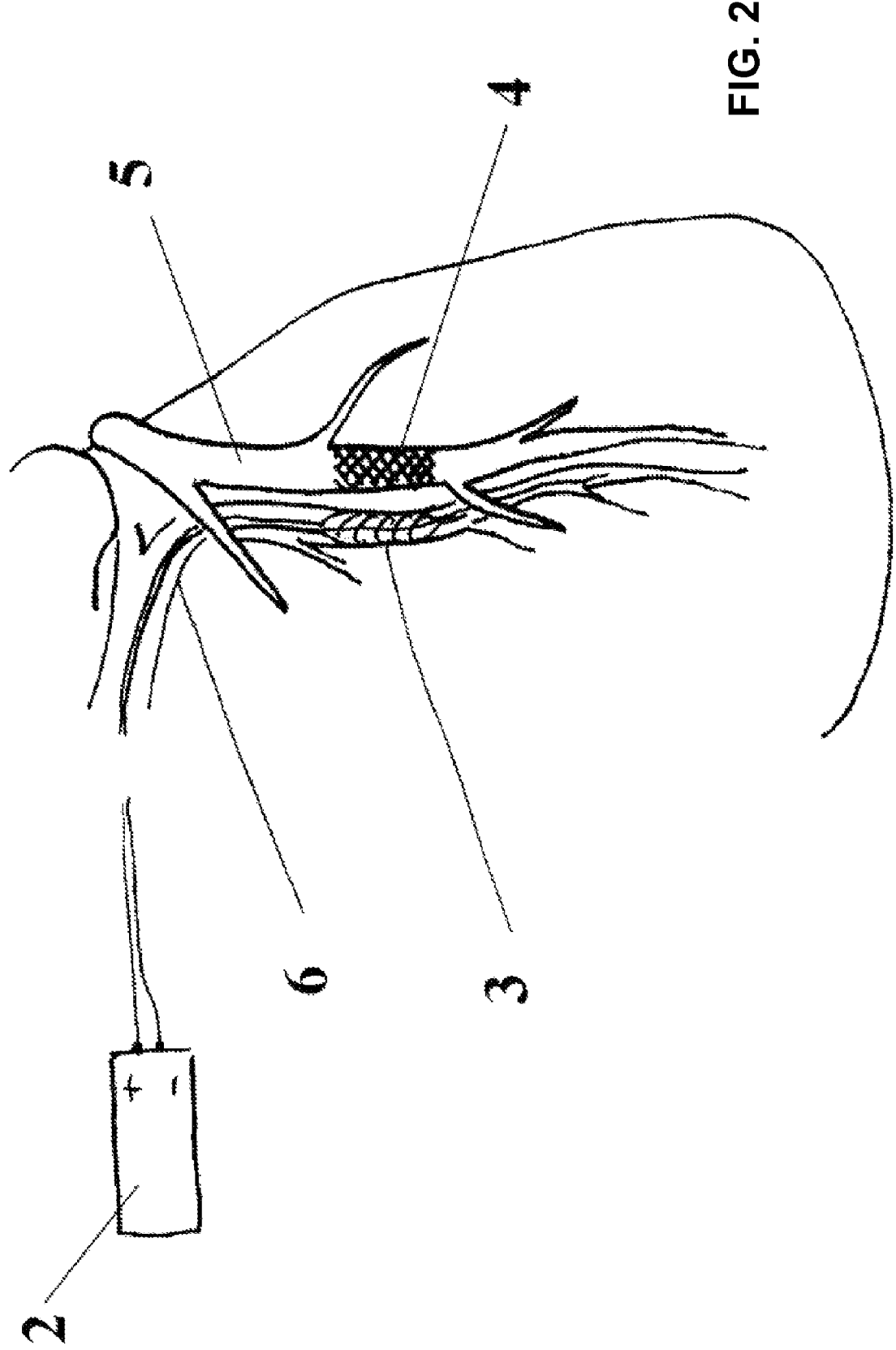
FIG. 2 demonstrates one of alternatives for reducing the distance from a source of a magnetic field; in this case the role of such source is played by temporary magnetic catheter 3, and stent 4.
Figure 3:
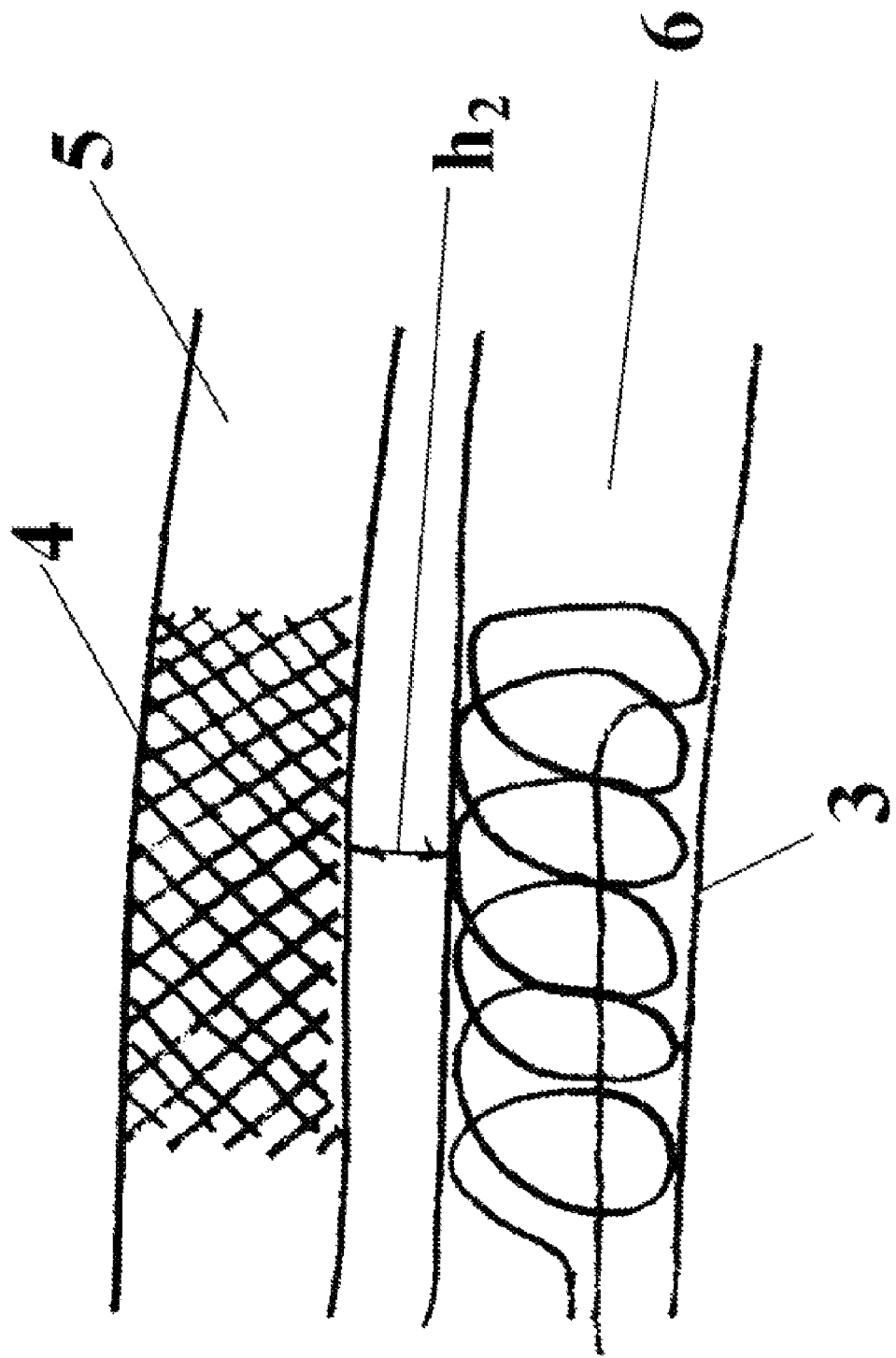
FIG. 3 demonstrates reduction of the distance between stent 4 implanted in cardiac artery 5, and temporary magnetic catheter 3 introduced into cardiac vein 6. Here, distance h2 between the source of the magnetic field, i.e., temporary magnetic catheter 3, and stent 4, is within, on the average, 1 mm.
Figure 4:
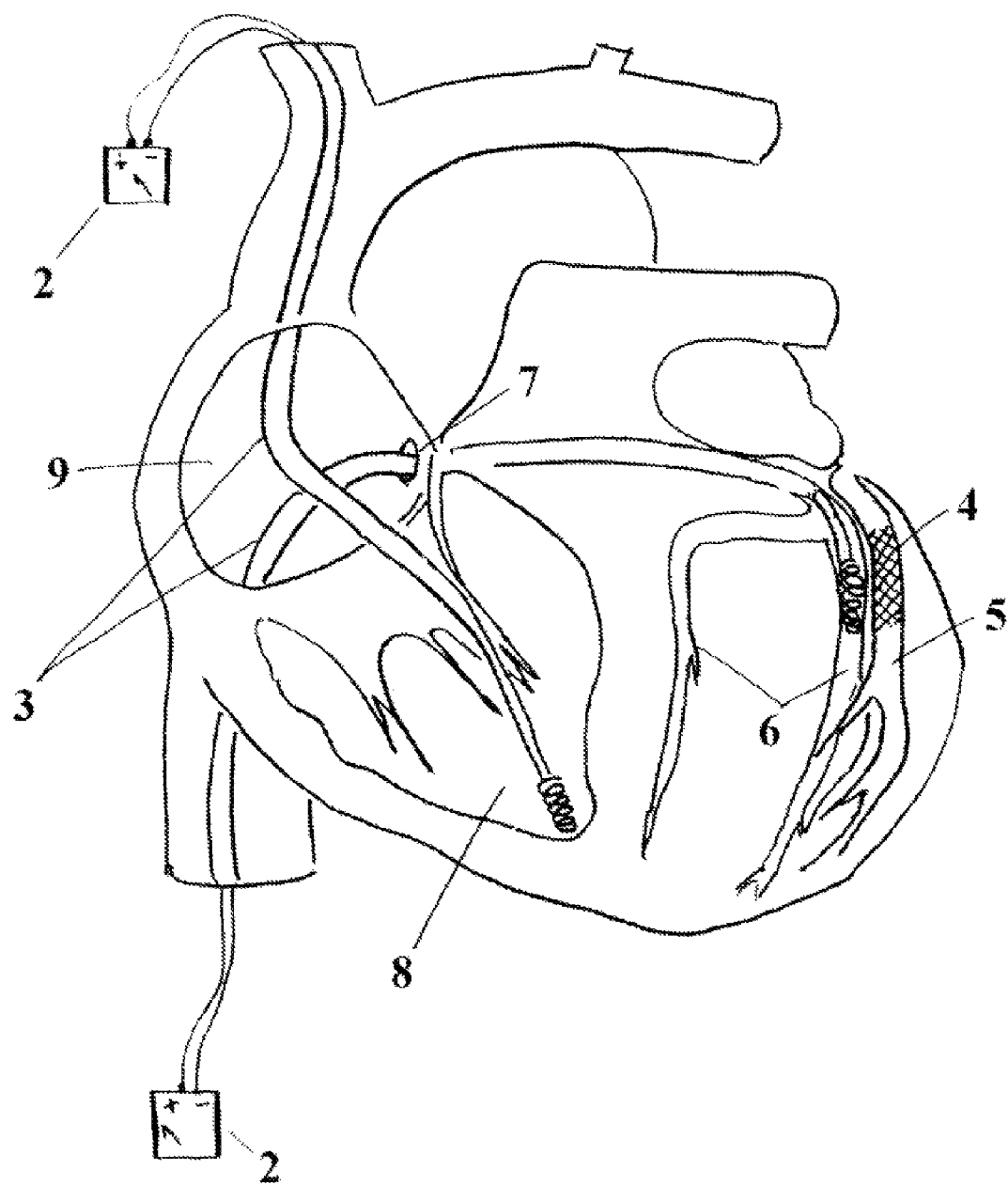
FIG. 4 presents an alternative method of localization of temporary catheters 3 and stent 4 at preventive treatment of coronary restenosis, where 7 is a coronary sine, 8 is the right ventricle of a heart, 9 is the right atrium.

The claimed method is carried out as follows:

Before stent implantation, the catheter (not shown in the figures) is introduced in that area of the vascular wall which is assigned for the local drug treatment affecting, the catheter carries an intravascular mesh implant, i.e., stent 4 made of a paramagnetic material, for example—steel 316L or other alloys, in particular, cobalt-chromium alloys, cobalt-nickel alloys, and other materials with paramagnetic properties, and also composite materials. Practically any of stents commonly used in a clinical practice can be used in this method.

After installation of stent 4 the catheter is removed, and, through the right atrium and coronary sinus 7, at least one temporary catheter 3 with the permanent magnet or the solenoid affixed at its distal end is introduced in coronary vein 6 and/or in right ventricle 8. The role of such permanent magnet is played by a cylindrical or conical piece of iron, cobalt, nickel, or their alloys, rare earth, magnetic ceramics or polymers filled with particles of the above materials. It is preferable to use the neodymium permanent magnets (NdBFe). In another alternative, the distal end of catheter 3 can carry a solenoid with a core, connected to electric power source 2. The core also can have a shape of a cylinder or can be provided with a conical cap, and the intensity of the gradient magnetic field is controlled by adjustment of the electrical current in the solenoid.

Thus, an endovascular source of a gradient permanent magnetic field, temporarily located in cardiac chambers or/and in the cardiac veins, is created, thereby distance h2 between the source and stent 4 made of magneto-responsive material is substantially reduced and, accordingly, distance between the source and the intravascular area of drug treatment. Experiments confirmed that the optimal alternative consists in designing the distal end of the temporary catheter in the shape of a cylindrical permanent magnet or a solenoid with length range of 1 to 50 mm, thereby achieving an essential decrease (reduction) of working magnetic field intensity to the safety level for a patient.

The distance between the distal end of the temporary catheter and the intravascular stent can thus be reduced to 1 mm. Furthermore, the magnetization of the intravascular stent is maintained only during presence of the gradient permanent magnetic field with the induction level not exceeding 1 Tesla. By means of the controlled current source, it is possible to control the parameters of the magnetic field induced by a solenoid in the area of local drug administering, and, accordingly, to control the level of adhesion of drugs to a vascular wall in the area of implantation of the paramagnetic stent.

Figure 5:
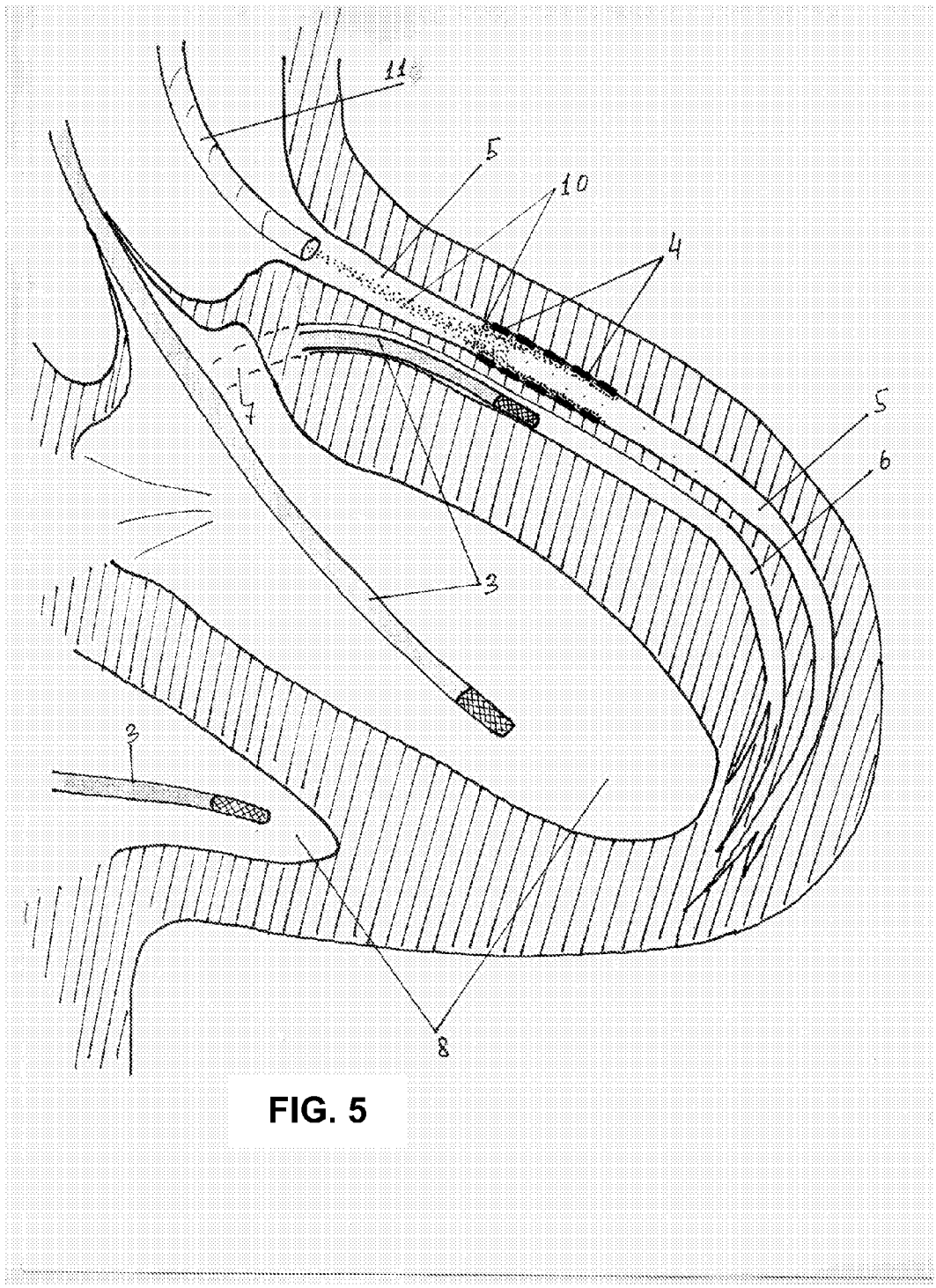
FIG. 5 shows the final stage of the method, where magnetic catheters 3 are positioned in ventricles of heart 8 and coronary vein 6 beforehand, and stent 4 is implanted into the coronary artery 5. Suspension 10 of magneto-responsive particles through guiding catheter 11 is injected in the coronary channel, where, under the force of the gradient magnetic field generated by catheter 3, the particles are accumulated in the area of location of the paramagnetic stent.

At the final stage of the method a magneto-responsive polymeric carrying agent, i.e., the suspension of particles whose size is, preferably, within the range 0.1-1.0 micron, containing a drug, is injected into a vascular channel. Under the force of a gradient permanent magnetic field, the magneto-responsive polymeric particles are concentrated in the area of the stent, thus rendering the targeted drug treatment of the arterial wall, as shown in FIG. 5. The temporary catheters with permanent magnets or solenoids are then removed, and no residual magnetization remains on the stent.

Having thus described a preferred embodiment, it should be apparent to those skilled in the art that certain advantages of the described method and apparatus have been achieved. It should also be appreciated that various modifications, adaptations, and alternative embodiments thereof may be made within the scope and spirit of the present invention. The invention is further defined by the following claims.

What is claimed is:

1. A method for endovascular magnetic targeting drug delivery in a vascular wall and adjoining tissues, comprising:
    implanting an endovascular mesh stent with paramagnetic properties in an area of interest by using a first catheter;
    injecting a polymeric magneto-responsive carrying agent in a form of particles, containing a drug;
    introducing at least one temporary catheter into a right atrium, and/or in ventricles of heart, and/or in a coronary sinus, and/or in a coronary vein, such that a distal end of the temporary catheter is positioned in proximity to the implanted endovascular mesh stent;
    generating a magnetic field at the area of interest using the temporary catheter;
    adjusting the magnetic field by means of a permanent magnet and/or a solenoid with the core, connected to an electric power source, wherein the permanent magnet and/or the solenoid is at the distal end of the at least one temporary catheter, and wherein a maximum magnetic field is at the implanted endovascular mesh stent; and
    removing the magnetic field to return the implanted endovascular mesh stent to a non-magnetized state,
    wherein a size of particles of the polymeric magneto-responsive carrying agent is between 0.01-1.0 microns, and
    wherein the magnetic field has a strength of no more than 1 Tesla.

2. The method of claim 1, wherein the magnetic field is produced by a permanent magnet of a cylindrical shape.

3. The method of claim 2, wherein the cylindrical shape has a cone-shaped cap.

4. The method of claim 1, wherein the magnetic field has a strength of at least 0.001 Tesla.

5. The method of claim 1, wherein the magnetic field is produced by a solenoid having a core of a cylindrical shape.

6. The method of claim 1, wherein the solenoid has a cone-shaped cap.

7. The method of claim 1, wherein the magnetic field is controlled by the adjusting an electric current through the solenoid.

8. The method of claim 1, wherein the endovascular mesh stent is made of a paramagnetic material.

9. The method of claim 1, wherein the endovascular mesh stent is made of a composite biodegradable material with paramagnetic properties.

10. The method of claim 1, wherein the temporary catheter has, at its distal end, a solenoid with length between 1 and 50 mm.

11. The method of claim 1, wherein the temporary catheter and the magneto-sensitive agent are introduced immediately after the endovascular mesh stent implantation.

12. The method of claim 1, wherein the temporary catheter and the magneto-responsive carrying agent are introduced for a drug treatment of a vascular wall at any time after the endovascular mesh stent implantation.

13. A kit for endovascular magnetic targeting drug delivery in a vascular wall and adjoining tissues, comprising:
    an endovascular mesh stent with paramagnetic properties implantable in an area of interest by using a first catheter;
    a polymeric magneto-responsive carrying agent in a form of particles, containing a drug injectable into an area of interest;
    at least one temporary catheter for introduction into a right atrium, and/or in ventricles of heart, and/or in a coronary sinus, and/or in a coronary vein, such that a distal end of the temporary catheter is positionable in proximity to the implanted endovascular mesh stent;
    wherein the temporary catheter is adapted to generate a magnetic field at the area of interest; and
    wherein the magnetic field is adjustable by means of a permanent magnet and/or a solenoid with the core, connected to an electric power source, wherein the permanent magnet and/or the solenoid is at the distal end of the at least one temporary catheter, and wherein a maximum magnetic field is at the implanted endovascular mesh stent;
    wherein the implanted endovascular mesh stent, upon withdrawal of the temporary catheter, returns to a non-magnetized state,
    wherein a size of the particles is between 0.01-1.0 microns, and
    wherein the magnetic field has a strength of no more than 1 Tesla.

14. The kit of claim 13, wherein the magnetic field is produced by a permanent magnet of a cylindrical shape.

15. The kit of claim 14, wherein the cylindrical shape has a cone-shaped cap.

16. The kit of claim 13, wherein the magnetic field has a strength of at least 0.001 Tesla.

17. The kit of claim 13, wherein the magnetic field is produced by a solenoid having a core of a cylindrical shape.

18. The kit of claim 13, wherein the solenoid has a cone-shaped cap.

19. The kit of claim 13, wherein the magnetic field is controlled by the adjusting an electric current through the solenoid.

20. The kit of claim 13, wherein the endovascular mesh stent is made of a composite biodegradable material with paramagnetic properties.

* * * * *